(12) United States Patent
An et al.

(10) Patent No.: US 11,377,659 B2
(45) Date of Patent: Jul. 5, 2022

(54) SHORT HAIRPIN RNA (SHRNA734) AND USE OF SAME TO POSITIVELY SELECT AND ELIMINATE GENETICALLY MODIFIED CELLS

(71) Applicant: THE REGENTS OF THE UNIVERSITY OF CALIFORNIA, Oakland, CA (US)

(72) Inventors: Dong Sung An, Los Angeles, CA (US); Saki Shimizu, Berkeley, CA (US)

(73) Assignee: THE REGENTS OF THE UNIVERSITY OE CALIFORNIA, Oakland, CA (US)

( * ) Notice: Subject to any disclaimer, the term of this patent is extended or adjusted under 35 U.S.C. 154(b) by 211 days.

(21) Appl. No.: 15/999,854

(22) PCT Filed: Feb. 17, 2017

(86) PCT No.: PCT/US2017/018483
§ 371 (c)(1),
(2) Date: Aug. 20, 2018

(87) PCT Pub. No.: WO2017/143266
PCT Pub. Date: Aug. 24, 2017

(65) Prior Publication Data
US 2021/0310007 A1    Oct. 7, 2021

Related U.S. Application Data

(60) Provisional application No. 62/297,432, filed on Feb. 19, 2016.

(51) Int. Cl.
*C12N 15/113*      (2010.01)
*C12N 5/00*        (2006.01)
(Continued)

(52) U.S. Cl.
CPC .......... *C12N 15/1137* (2013.01); *A61K 35/28* (2013.01); *A61K 45/06* (2013.01);
(Continued)

(58) Field of Classification Search
None
See application file for complete search history.

(56) References Cited

U.S. PATENT DOCUMENTS 7,737,124 B2 * 6/2010 Lois-Caballe .......... A61P 31/18
                                                    514/44 R
10,961,537 B2 * 3/2021 Ahlers ................. C12N 9/1077
(Continued)

FOREIGN PATENT DOCUMENTS

WO    WO1997043900 A1    11/1997
WO    WO1998019540 A1    5/1998
(Continued)

OTHER PUBLICATIONS

Choudhary, Rashmi et al.: "Knockdown of HPRT for selection of genetically modified human hematopoietic progenitor cells", PLOS One, vol. 8, No. 3, Mar. 15, 2013, p. e59594, and supplemental pages.
(Continued)

*Primary Examiner* — Arthur S Leonard
(74) *Attorney, Agent, or Firm* — Karen S. Canady; canady + lortz LLP

(57) ABSTRACT

A potent short hairpin RNA (shRNA734) directed to human Hypoxanthine Guanine Phosphoribosyltransferase (HPRT) improves the rate of gene-modified stem cell engraftment by a conditioning and in vivo selection strategy to confer resistance to a clinically available guanine analog antimetabolite, 6TG, for efficient positive selection of gene-modified stem cells. Uses for polynucleotides comprising the shRNA734 include methods for knocking down HPRT in a
(Continued)

cell, for conferring resistance to a guanine analog antimetabolite in a cell, for producing selectable genetically modified cells, for selecting cells genetically modified with a gene of interest from a plurality of cells, for removing cells genetically modified with a gene of interest from a plurality of cells, and for treating a subject infected with HIV.

20 Claims, 6 Drawing Sheets

Specification includes a Sequence Listing.

(51) Int. Cl.
  *A61K 35/28* (2015.01)
  *A61K 45/06* (2006.01)
  *C12N 15/86* (2006.01)
(52) U.S. Cl.
  CPC ........... *C12N 5/0081* (2013.01); *C12N 15/86* (2013.01); *C12N 2310/531* (2013.01); *C12N 2740/15043* (2013.01); *C12Y 204/02008* (2013.01)

(56) References Cited

U.S. PATENT DOCUMENTS

| | | | |
|---|---|---|---|
| 2003/0032003 | A1 | 2/2003 | Schiestl et al. |
| 2005/0255487 | A1* | 11/2005 | Khvorova ............... A61P 21/00 435/6.11 |
| 2005/0266552 | A1 | 12/2005 | Doench et al. |
| 2008/0120733 | A1 | 5/2008 | Hafner et al. |

FOREIGN PATENT DOCUMENTS

| | | |
|---|---|---|
| WO | WO0240049 A1 | 5/2002 |
| WO | WO2005056761 A2 | 6/2005 |
| WO | WO2008076370 A2 | 6/2008 |
| WO | WO2008109837 A2 | 9/2008 |
| WO | WO2012061075 A2 | 5/2012 |
| WO | WO2014114934 A1 | 7/2014 |
| WO | WO2015017755 A1 | 2/2015 |

OTHER PUBLICATIONS

Guibinga, Ghiabe-Henri et al.: "Deficiency of the housekeeping gene Hypoxanthine-Guanine Phosphoribosyltransferase (HPRT) dysregulates neurogenesis", Molecular Therapy, vol. 18, No. 1, Jan. 1, 2010, pp. 54-62.
Kang, Tae Hyuk et al.: "HPRT deficiency coordinately dysregulates canonical Wnt and Presenilin-1 signaling: a neuro-developmental regulatory role for a housekeeping gene?", PLOS ONE, vol. 6, No. 1, Jan. 28, 2011, p. e16572.
Mastrangelo, L. et al.: "Purinergic signaling in human pluripotent stem cells is regulated by the housekeeping gene encoding Hypoxanthine Guanine Phosphoribosyltransferase", Proceedings of the National Academy of Sciences (PNAS) USA, vol. 109, No. 9, Feb. 13, 2012, pp. 3377-3382.
Narukawa, M., et al.,"Efficient selection of genetically engineered HIV resistant cells by short hairpin RNA mediated HPRT and CCR5 knockdown.",Molecular Therapy,2013year 5 month and vol. 21, No. suppl.1,S204,[503].
Narukawa, M., et al.,"Efficient selection of genetically engineered HIV resistant cells by short hairpin RNA mediated HPRT and CCR5 knockdown.",International Journal of Antimicrobial Agents,2013, vol. 42S2,p. S128,[P274].
Zhang, J. et al: "Silencing p21 waf1/Cip1/Sdi1 expression increases gene transduction efficiency in primitive human hematopoietic cells", Gene Therapy, Oct. 1, 2005, pp. 1444-1452.
Examination Report received in co-pending EP Application 17753977. 2, dated Oct. 26, 2020.
Office Action received in co-pending JP Application 2018-543719, dated Feb. 2, 2021, with machine translation in English.
Aubrecht, J. et al., "Tissue Specific Toxicities of the Anticancer Drug 6-Thioguanine Is Dependent on the Hprt Status in Transgenic Mice", J. Pharm. Exp. Ther. 1997, 282(2):1102-1108.
Boyd, Diana, et al. Functional Redundancy of Promoter Elements Ensures Efficient Transcription of the Human 7SK Gene in vivo. J. Mol. Biol. (1995) 253, 677-690.
Choudhary, Rashimi, et al., Knockdown of HPRT Enables Selection of Genetically Modified Human Hematopoietic Progenitor Cells. Blood 2010 116:3772.
Choudhary, Rashimi, et al., Knockdown of HPRT Enables Selection of Genetically Modified Human Hematopoietic Progenitor Cells. PLoS ONE 8(3): e59594. doi:10.1371/journal.pone.0059594, 2013.
Delicou, S. et al., "Successful HLA-identical hematopoietic stem cell transplantation in a patient with purine nucleoside phosphorylase deficiency", Pediatric Transplantation, 2007, 11:799-803.
Foss, F. M. et al., "The Role of Purine Analogues in Low-Intensity Regimens With Allogeneic Hematopoietic Stem Cell Transplantation", Semin. Hematol. 2006, 43(suppl 2):S35-S43.
Giralt, Sergio, et al., "Engraftment Of Allogenic Hematopoietic Progenitor Cells With Purine Analog-Containing Chemotherapy: Harnessing Graft-Versus-Leukemia Without Myeloablative Therapy", Jun. 15, 1997, pp. 4531-4536, XP002101604, vol. 89, No. 12, Publisher: Blood, American Society of Hematology, Published in: United States.
Guibinga, Ghiabe-Henri, et al., Deficiency of the Housekeeping Gene Hypoxanthine-Guanine Phosphoribosyltransferase (HPRT) Dysregulates Neurogenesis. Molecular Therapy vol. 18, Issue 1, Jan. 2010, pp. 54-62. https://doi.org/10.1038/mt.2009.178.
Hacke, K., "Combined preconditioning and in vivo chemoselection with 6-thioguanine alone achieves highly efficient reconstitution of normal hematopoiesis with HPRT-deficient bone marrow", Exp. Hematol., 2012, 403: 3-13.
Hacke, Katrin, et al. Genetic modification of mouse bone marrow by lentiviral vector-mediated delivery of HPRT shRNA confers chemoprotection against 6-thioguanine cytotoxicity. Transplant Proc. Jun. 2013 ; 45(5): 2040-2044. doi:10.1016/j.transproceed.2013.01. 020.
Neff, T . . . et al., "Survival of the fittest: in vivo selection and stem cell gene therapy", Blood, 2006, 107:1751-1760.
Porter, Christopher C., et al., Interfering RNA-mediated purine analog resistance for in vitro and in vivo cell selection. Blood, Dec. 1, 2008 vol. 112, No. 12: 4466-4474.
Shimizu, Saki, et al. Stable Delivery of CCR5-Directed shRNA into Human Primary Peripheral Blood Mononuclear Cells and Hematopoietic Stem/Progenitor Cells via a Lentiviral Vector. Methods Mol Biol. 2016;1364:235-48. doi: 10.1007/978-1-4939-3112-5_19.
International Search Report for PCT/US17/18483 (WO2017143266 Published Aug. 24, 2017).

* cited by examiner

CCR5 shRNA & HPRT shRNA vector (EGFP)

Days post 6TG ex vivo selection

SEQUENCE LISTING

<160> NUMBER OF SEQ ID NOS: 5

<210> SEQ ID NO 1
<211> LENGTH: 47
<212> TYPE: DNA
<213> ORGANISM: Artificial Sequence
<220> FEATURE:

<223> OTHER INFORMATION: shRNA coding sequence

<400> SEQUENCE: 1
aggatatgcc cttgactatt tgtccgacat agtcaagggc atatcct        47

<210> SEQ ID NO 2
<211> LENGTH: 51
<212> TYPE: DNA
<213> ORGANISM: Artificial Sequence
<220> FEATURE:
<223> OTHER INFORMATION: shRNA coding sequence

<400> SEQUENCE: 2
agagcaagct cagtttacac cttgtccgac ggtgtaaact gagcttgctc t        51

<210> SEQ ID NO 3
<211> LENGTH: 243
<212> TYPE: DNA
<213> ORGANISM: Homo sapiens

<400> SEQUENCE: 3
ctgcagtatt tagcatgccc acccatctg caaggcattc tggatagtgt caaaacagcc        60
ggaaatcaag tccgtttatc tcaaacttta gcattttggg aataaatgat atttgctatg        120
ctggttaaat tagattttag ttaaatttcc tgctgaagct ctagtacgat aagcaacttg        180
acctaagtgt aaagttgaga tttccttcag gtttatatag cttgtgcgcc gcctgggtac        240
ctc        243

<210> SEQ ID NO 4
<211> LENGTH: 243
<212> TYPE: DNA
<213> ORGANISM: Homo sapiens

<400> SEQUENCE: 4
ctgcagtcgg gctactgccc acccatagt accggcattc tggatagtgt caaaacagcc        60
ggaaatcaag tccgtttatc tcaaacttta gcattttggg aataaatgat atttgctatg        120
ctggttaaat tagattttag ttaaatttcc tgctgaagct ctagtacgat aagcaacttg        180
acctaagtgt aaagttgaga tttccttcag gtttatatag cttgtgcgcc gcctgggtac        240
ctc        243

<210> SEQ ID NO 5
<211> LENGTH: 243
<212> TYPE: DNA
<213> ORGANISM: Homo sapiens

<400> SEQUENCE: 5
ctgcagtmkk kmkmmtgccc acccatmkk mmmggcattc tggatagtgt caaaacagcc        60
ggaaatcaag tccgtttatc tcaaacttta gcattttggg aataaatgat atttgctatg        120
ctggttaaat tagattttag ttaaatttcc tgctgaagct ctagtacgat aagcaacttg        180
acctaagtgt aaagttgaga tttccttcag gtttatatag cttgtgcgcc gcctgggtac        240
ctc        243

SHORT HAIRPIN RNA (SHRNA734) AND USE OF SAME TO POSITIVELY SELECT AND ELIMINATE GENETICALLY MODIFIED CELLS

This application claims benefit of U.S. provisional patent application No. 62/297,432, filed Feb. 19, 2016, the entire contents of which are incorporated by reference into this application.

STATEMENT REGARDING FEDERALLY SPONSORED RESEARCH

This invention was made with Government support under AI028697, AI117941, awarded by the National Institutes of Health. The Government has certain rights in the invention.

REFERENCE TO A SEQUENCE LISTING SUBMITTED VIA EFS-WEB

The content of the ASCII text file of the sequence listing named "UCLA239WOU1_SL", which is 3 kb in size, was created on Feb. 17, 2017, and electronically submitted via EFS-Web herewith the application. The sequence listing is incorporated herein by reference in its entirety.

TECHNICAL FIELD OF THE INVENTION

The present invention relates to nucleic acid molecules, including a short hairpin ribonucleic acid molecule (shRNA) and polynucleotides comprising and/or encoding same, that can be used to knock down (e.g., silence expression of) hypoxanthine guanine phosphoribosyltransferase (HPRT), as well as methods of using same. The methods include, for example, a method for knocking down HPRT in a cell, a method for conferring resistance to a guanine analog antimetabolite in a cell, a method for producing selectable genetically modified cells, a method for selecting cells genetically modified with a gene of interest from a plurality of cells, a method for removing cells genetically modified with a gene of interest from a plurality of cells, and methods for treating a subject having a disease or condition, such as a subject infected with HIV.

BACKGROUND OF THE INVENTION

Gene therapy strategies to modify human stem cells hold great promise for curing many human diseases. However, previous clinical studies have met with limited success, largely due to the low engraftment of gene modified stem cells. One strategy to overcome this challenge involves engineering stem cells in which HPRT expression is knocked down, thereby facilitating the selection of genetically modified cells by conferring resistance to a guanine analog antimetabolite.

While efforts have been made to disrupt HPRT, there remains a need for more effective materials and methods to directly target the HPRT gene.

SUMMARY

The invention meets these needs and others by providing a polynucleotide comprising a short hairpin ribonucleic acid molecule 734 (shRNA734) and methods of using same. The invention provides a small RNA based chemoselection strategy that can be used for improving the engraftment of genetically modified cells for stem cell based gene therapy strategies.

In a typical embodiment, the shRNA734 nucleic acid coding sequence is SEQ ID NO: 1. In some embodiments, the polynucleotide further comprises an expression control sequence. In some embodiments, the expression control sequence comprises a 5' long terminal repeat (LTR) upstream of the shRNA and a 3' LTR downstream of the shRNA734.

In one embodiment, the polynucleotide further comprises a gene of interest disposed downstream of the 5' LTR and upstream of the shRNA734. In one embodiment, the gene of interest is an inhibitor of CCR5. One example of a CCR5 inhibitor is SEQ ID NO: 2 (CCR5shRNA). In one embodiment, the polynucleotide is a viral vector. A representative embodiment of the polynucleotide having a CCR5shRNA is the vector shown in FIG. 1, wherein H1 is human H1 RNA promoter; UbC is human ubiquitin promoter; 7SK is human 7SK RNA promoter; GFP is green fluorescent protein; C46 is HIV fusion inhibitor. In some embodiments, GFP and/or C46 is replaced with an alternative gene of interest, such as a therapeutic gene. Also provided is a pharmaceutical composition comprising the polynucleotide described above.

The invention additionally provides a method for knocking down hypoxanthine guanine phosphoribosyltransferase (HPRT) in a cell. In one embodiment, the method comprises contacting the cell with a polynucleotide as described herein under conditions permitting expression of SEQ ID NO: 1 in the cell.

The invention further provides a method for conferring resistance to a guanine analog antimetabolite in a cell. In one embodiment, the method comprises contacting the cell with a polynucleotide of the invention under conditions permitting expression of SEQ ID NO: 1 in the cell. In one embodiment, the guanine analog antimetabolite is 6-thioguanine (6TG).

Another method provided by the invention is a method for producing selectable genetically modified cells. In one embodiment, the method comprises contacting a plurality of cells with a polynucleotide of the invention under conditions permitting expression of the gene of interest and SEQ ID NO: 1. In one embodiment, the method further comprises removing unmodified cells from the plurality of cells. The removing comprises treating the plurality of cells contacted with the polynucleotide with a guanine analog antimetabolite. In another embodiment, the method further comprises removing the genetically modified cells from the plurality of cells. The removing comprises treating the plurality of cells with methotrexate (MTX).

The invention further provides a method for selecting cells genetically modified with a gene of interest from a plurality of cells. In one embodiment, the method comprises contacting a plurality of cells that comprises genetically modified cells, wherein the genetically modified cells have been modified with a polynucleotide of the invention under conditions permitting expression of the gene of interest and SEQ ID NO: 1. The method further comprises removing unmodified cells from the plurality of cells. The removing comprises treating the plurality of cells contacted with the polynucleotide with a guanine analog antimetabolite.

Also provided is a method for removing cells genetically modified with a gene of interest from a plurality of cells. In one embodiment, the method comprises contacting a plurality of cells that comprises genetically modified cells, wherein the genetically modified cells have been modified with a polynucleotide of the invention under conditions permitting expression of the gene of interest and SEQ ID NO: 1. The method further comprises removing the genetically modified cells from the plurality of cells. The removing comprises treating the plurality of cells with methotrexate (MTX).

The invention additionally provides a method for treating a subject infected with HIV. In one embodiment, the method comprises contacting a plurality of hematopoietic stem/progenitor cells (HSPCs) that have been modified with a polynucleotide of the invention under conditions permitting expression of the gene of interest and SEQ ID NO: 1. The method further comprises treating the plurality of cells contacted with the polynucleotide with a guanine analog antimetabolite to form a purified population of genetically modified cells; and administering the purified population of genetically modified cells to the subject.

DETAILED DESCRIPTION OF THE INVENTION

Figure 1:
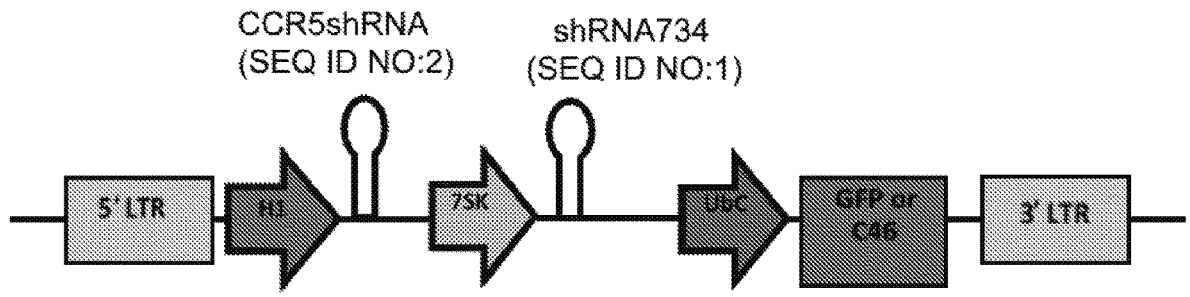
FIG. 1. Schematic illustration of a representative lentiviral vector comprising CCR5 shRNA and HPRT shRNA.
Figure 2:
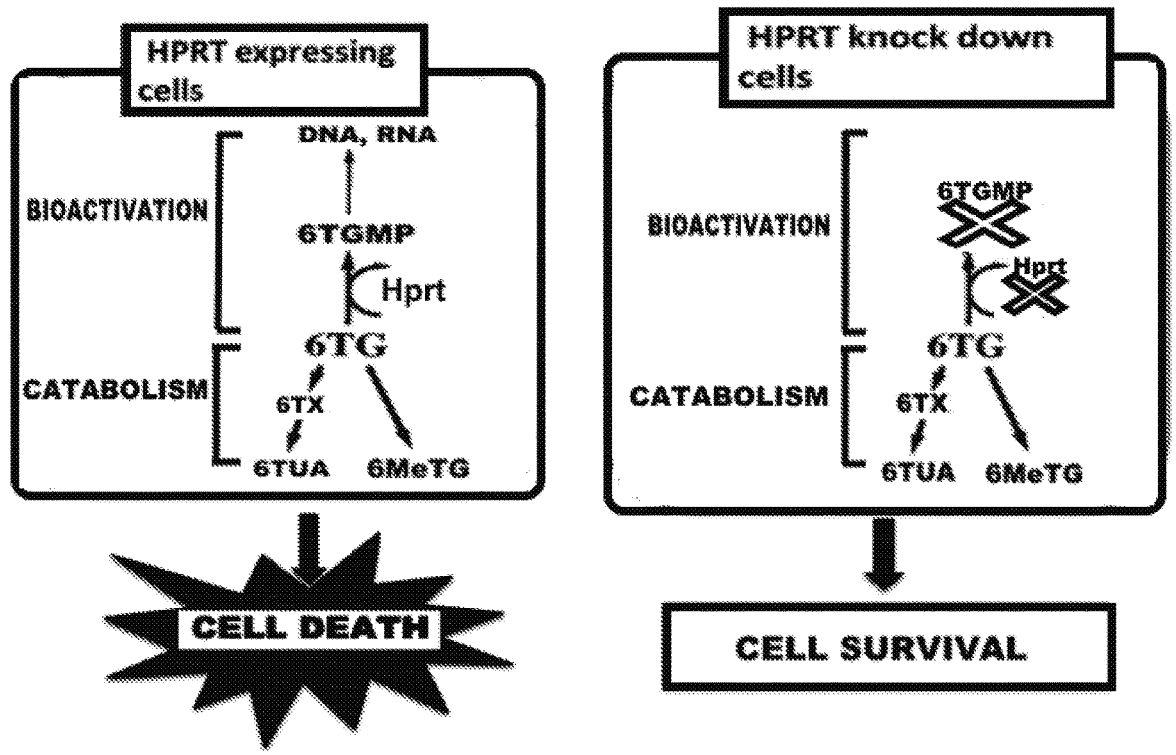
FIG. 2. Schematic illustration of metabolic pathways involved in HPRT expression and knock down.
Figure 3:
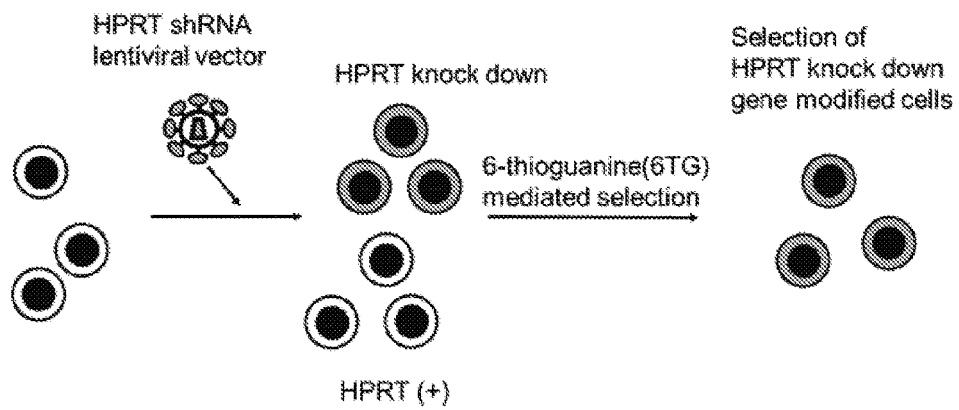
FIG. 3. Schematic illustration of HPRT deficient cells positively selected by 6TG.

The novel and potent short hairpin RNA (shRNA734) directed to human Hypoxanthine Guanine Phosphoribosyltransferase (HPRT) described herein improves the rate of gene-modified stem cell engraftment by use of a conditioning and in vivo selection strategy to confer resistance to a clinically available guanine analog antimetabolite, 6TG, for efficient positive selection of gene-modified stem cells. 6TG is metabolized by HPRT, and the active toxic metabolite is incorporated into DNA and RNA and causes cytotoxicity. shRNA734-mediated HPRT knockdown can prevent the formation of the active toxic metabolite and enable selection of shRNA734 gene modified HPRT knockdown stem cells.

For example, a lentiviral vector mediated co-delivery of anti-HIV genes and shRNA734 can result in stable knockdown of HPRT in human stem cells, and these gene-modified stem cells transplanted with 6TG preconditioning and chemoselection can improve engraftment of HIV protected stem cells to achieve stable control of HIV infection. The gene-modified cells were able to block HIV-1 of both R5 and X4 tropism. Furthermore, in addition to the positive selection, a novel feature of the shRNA734-mediated HPRT knockdown strategy is that it can be used as a negative selection to eliminate the HPRT deficient cells by using methotrexate (MTX) to inhibit the enzyme dihydrofolate reductase (DHFR) in the purine de novo synthetic pathway. Thus, it can be developed as a safety procedure to eliminate gene-modified HSPC in case of unexpected adverse effects observed.

The potent and non-toxic HPRT shRNA enables 6TG-mediated positive selection of lentiviral vector-transduced human T-cell line, CD34+ cells and primary peripheral blood mononuclear cells (PBMC) in vitro. A lentivirus vector was utilized to deliver sh734 and to stably knockdown HPRT in human T cell lines, primary peripheral blood mononuclear cells and CD34+ hematopoietic stem/progenitor cells. There was efficient HPRT knockdown leading to resistance to 6TG. Vector transduced cells were positively selected for in the presence of 6TG.

To test an application of shRNA734 to an anti-HIV-1 stem cell based gene therapy, sh734 and sh1005 (a shRNA directed to CCR5 HIV co-receptor) co-expression from a lentiviral vector efficiently down regulated CCR5 and HPRT expression. The initial in vivo engraftment experiment of the dual sh1005/HPRT shRNA vector modified human HSPC shows reconstitution of CCR5 down-regulated human T-cells in humanized BLT mice. Ex vivo isolated splenocytes from the BLT mice were positively selected by 6TG.

Furthermore, the invention provides a combinatorial anti-HIV lentiviral vector expressing the HIV fusion inhibitor C46, and shRNAs for CCR5 and HPRT. Vector transduced human cell lines (K562, CCR5 MT-4) were positively selected with 6TG, in vitro. More importantly primary PBMC and fetal liver derived CD34+ cells can also be positively selected with 6TG. In addition, HPRT expression was efficiently knocked down in 6TG selected cells as measured by Western Blot. Methotrexate (MTX) has been used to negatively select the transduced cells. Finally, 6TG selected anti-HIV (CCR5 shRNA and C46) vector transduced CCR5 MT-4 cells were shown to be resistant to HIV infection in vitro.

These results demonstrate that this newly identified HPRT shRNA can be combined with the CCR5 directed shRNA (sh1005) and C46 in a lentiviral vector for efficient positive selection.

In addition to the positive selection strategy, using MTX negatively selected human T-cell line and CD34+ cells expressing shRNA734 in vitro.

Advantages

This RNA based technology has advantages over existing in vivo selection strategies. Previous in vivo selection strategies employing various drug resistance genes have been tested, but have been associated with unacceptable toxicity or insufficient selection efficiency. Notably, these approaches have generally relied upon transplantation of HSPCs overexpressing an exogenous drug resistance gene into recipients preconditioned with myeloablative irradiation.

One successful example of this approach to date employs the P140K mutant form of human $O^6$-methylguanine-DNA-methyltransferase (MGMT P140K), which confers resistance to $O^6$-benzylguanine ($O^6$BG) and DNA damaging agents, such as 1,3-bis (2-chloroethyl)-1-nitrosurea (BCNU). MGMT P140K expressed from retro/lentiviral vectors enables selection of transduced HSPC in mice, non-human primates and is being tested in clinical trials for myeloprotection in glioblastoma patients. However, high level MGMT P140K expression has been reported to cause cytotoxicity in itself, and more generally, the potential immunogenicity of the exogenous drug resistance transgene protein products is a concern.

Recently, in vivo MGMT selection was applied for a C46 mono anti-HIV expressing vector modified HSPC transplant study in a pigtail macaque. However, the inclusion of relatively large MGMT P140K reduces available vector packaging capacity for additional anti-HIV genes, creates a complex vector genome and may reduce vector titers. Selection also requires the strong alkylating agent, BCNU.

In contrast, for the strategy described herein, chemo-resistance is conferred by a small and non-immunogenic shRNA that knocks down expression of an endogenous gene. Since gene therapy for HIV disease will require combinations of multiple therapeutic genes, decreasing the size of the vector using small RNAs is advantageous over large protein molecules. Furthermore, it would facilitate vector design and manufacturing. Chemoselection requires treatment with a purine analog antimetabolite, known to have less patient fertility issues than alkylating agents.

Definitions

All scientific and technical terms used in this application have meanings commonly used in the art unless otherwise specified. As used in this application, the following words or phrases have the meanings specified.

The term "nucleic acid" or "polynucleotide" or "oligonucleotide" refers to a sequence of nucleotides, a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, the term "active fragment" refers to a substantial portion of an oligonucleotide that is capable of performing the same function of specifically hybridizing to a target polynucleotide.

As used herein, the term "knockout" or "knocking down" refers to a genetic technique in which a target gene is made inoperative by disrupting and/or inactivating expression of the gene.

As used herein, "hybridizes," "hybridizing," and "hybridization" means that the oligonucleotide forms a noncovalent interaction with the target DNA molecule under standard conditions. Standard hybridizing conditions are those conditions that allow an oligonucleotide probe or primer to hybridize to a target DNA molecule. Such conditions are readily determined for an oligonucleotide probe or primer and the target DNA molecule using techniques well known to those skilled in the art. The nucleotide sequence of a target polynucleotide is generally a sequence complementary to the oligonucleotide primer or probe. The hybridizing oligonucleotide may contain non-hybridizing nucleotides that do not interfere with forming the noncovalent interaction. The nonhybridizing nucleotides of an oligonucleotide primer or probe may be located at an end of the hybridizing oligonucleotide or within the hybridizing oligonucleotide. Thus, an oligonucleotide probe or primer does not have to be complementary to all the nucleotides of the target sequence as long as there is hybridization under standard hybridization conditions.

The term "complement" and "complementary" as used herein, refers to the ability of two DNA molecules to base pair with each other, where an adenine on one DNA molecule will base pair to a thymine on a second DNA molecule and a cytosine on one DNA molecule will base pair to a guanine on a second DNA molecule. Two DNA molecules are complementary to each other when a nucleotide sequence in one DNA molecule can base pair with a nucleotide sequence in a second DNA molecule. For instance, the two DNA molecules 5'-ATGC and 5'-TACG are complementary, and the complement of the DNA molecule 5'-ATGC is 5'-TACG. The term complement and complementary also encompasses two DNA molecules where one DNA molecule contains at least one nucleotide that will not base pair to at least one nucleotide present on a second DNA molecule. For instance the third nucleotide of each of the two DNA molecules 5'-ATTGC and 5'-TATCG will not base pair, but these two DNA molecules are complementary as defined herein. Typically two DNA molecules are complementary if they hybridize under the standard conditions referred to above. Typically two DNA molecules are complementary if they have at least about 80% sequence identity, preferably at least about 90% sequence identity.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "vector" means a construct, which is capable of delivering, and preferably expressing, one or more gene(s) or sequence(s) of interest in a host cell.

As used herein, "a" or "an" means at least one, unless clearly indicated otherwise.

As used herein, to "prevent" or "protect against" a condition or disease means to hinder, reduce or delay the onset or progression of the condition or disease.

As used herein, the term "isolated" means that a naturally occurring DNA fragment, DNA molecule, coding sequence, or oligonucleotide is removed from its natural environment, or is a synthetic molecule or cloned product. Preferably, the DNA fragment, DNA molecule, coding sequence, or oligonucleotide is purified, i.e., essentially free from any other DNA fragment, DNA molecule, coding sequence, or oligonucleotide and associated cellular products or other impurities.

Polynucleotides and Methods of Using Same

The invention provides a short hairpin ribonucleic acid molecule (shRNA) and polynucleotides comprising same, that can be used to knock down (e.g., silence expression of) hypoxanthine guanine phosphoribosyltransferase (HPRT). In one embodiment, the invention provides a polynucleotide comprising a nucleic acid sequence encoding a shRNA734, wherein the shRNA734 nucleic acid sequence is SEQ ID NO: 1.

In one embodiment, the polynucleotide further comprises an expression control sequence. In one embodiment, the polynucleotide is a vector, such as, for example, a viral vector. In one embodiment, the expression control sequence comprises a 5' long terminal repeat (LTR) upstream of the shRNA and a 3' LTR downstream of the shRNA734. In one embodiment, the polynucleotide further comprises a gene of interest disposed downstream of the 5' LTR and upstream of the shRNA734. In one embodiment, the gene of interest is an inhibitor of CCR5. One example of an inhibitor of CCR5 is SEQ ID NO: 2 (CCR5shRNA).

In one embodiment, the vector comprises the elements represented in the schematic shown in FIG. 1, wherein:

H1 is human H1 RNA promoter (NCBI GenBank|S68670|H1 RNA gene {promoter} human, Genomic, 497 nt);

UbC is human ubiquitin promoter (Homo sapiens UbC gene for polyubiquitin, exon1-2, partial cds. Accession No. D63791) that can be used to drive expression of a gene of interest;

7SK is human 7SK RNA promoter (Homo sapiens cell-line HEK-293 7SK RNA promoter region, complete sequence. Accession No. AY578685, SEQ ID NO: 3; alternatively, the novel variant 7SK RNA promoter of SEQ ID NO: 4 or 5);

GFP is green fluorescent protein (NCBI GenBank|L29345|Aequorea victoria green-fluorescent protein (GFP) mRNA, complete cds.); and C46 is HIV fusion inhibitor (Egelhofer M, Brandenburg G, Martinius H, et al. Inhibition of human immunodeficiency virus type 1 entry in cells expressing gp41-derived peptides. J Virol 2004;78(2):568-575.)

A vector expressing both CCR5 and C46 provides two anti-HIV genes, which can be provided in conjunction with HPRT knock down and 6TG-mediated selection. Those skilled in the art will appreciate that an alternative gene of interest, such as a therapeutic gene, may be substituted for GFP and/or C46 in the vector. In one embodiment, the gene(s) of interest are up to 12 kb in length. In another embodiment, the gene(s) of interest comprise up to 3 or 4 genes in series. In a typical embodiment, cleaving peptides are disposed between the genes of interest.

The therapeutic gene(s) may be directed at HIV or another disease or condition. For example, the therapeutic gene(s) can be designed to correct a hereditary genetic defect, to alter drug sensitivity of normal bone marrow to cytotoxic drugs, to confer resistance to infectious microorganisms that affect lymphohematopoietic cells, to replace or re-set the endogenous immune system, or to combat lymphohematopoietic malignancies through replacement of endogenous bone marrow and induction of a graft-vs.-leukemia/lymphoma effect.

More specifically, hereditary genetic defects can include, but are not limited to, disorders of hematopoiesis including hemoglobinopathies such as sickle cell anemia, thalassemia, hereditary spherocytosis, G6PD deficiency, etc., disorders of immunologic or antimicrobial function such as severe combined immunodeficiency (SCID), chronic granulomatous disease (CGD), disorders of thrombopoiesis leading to coagulation defects such as Wiscott-Aldrich syndrome (WAS), as well as other genetic structural or metabolic disorders which can be ameliorated by genetic engineering of hematopoietic cells that travel to sites of tissue damage, such as various forms of epidermolysis bullosa (EB), and mucopolysaccharidosis.

Diseases in which modification of the drug sensitivity of bone marrow to chemotoxic drugs would be advantageous include, but are not limited to, malignant diseases that are treated by chemotherapy agents whose maximum tolerated dosage is limited by myelotoxicity. These include lung cancer, colorectal cancer, breast cancer, prostate cancer, pancreatic cancer, gastric cancer, liver cancer, head and neck cancer, renal cell carcinoma, bladder cancer, cervical cancer, ovarian cancer, skin cancer, sarcomas, and glioma.

Diseases in which bone marrow or hematopoietic stem cell transplantation is used to replace or reset the endogenous immune system include, but are not limited to, inflammatory bowel disease, scleroderma, and lupus erythematosis.

Diseases in which conferring resistance to infectious microorganisms would be advantageous include, but are not limited to, HIV infection and AIDS, HTLV infection, and parvovirus B19 infection.

Malignant or pre-malignant diseases of lymphohematopoiesis that are treated by bone marrow or hematopoietic stem cell transplantation include, but are not limited to, acute myelogenous leukemia, acute lymphocytic leukemia, lymphoma, and myelodysplastic syndromes.

Another example of the therapeutic application of this technology would be to improve the outcome of bone marrow or hematopoietic stem cell transplantation after acquired injury to endogenous lymphohematopoiesis caused by radiation injury, and chemotoxins.

A non-therapeutic but commercially useful application of this technology would be its use to generate humanized animal models, in which their endogenous lymphohematopoiesis is almost entirely replaced by cells from a human donor. Once generated, such animals could be used, for example, to test the myelotoxicity of new drugs being considered for application to human disease. This is advantageous because the sensitivity of hematopoiesis to various drugs can be different depending on the species of animal, therefore it is most desirable to test such drugs in a humanized animal model.

In one embodiment, the 7SK is SEQ ID NO: 3 (Homo sapiens cell-line HEK-293 7SK RNA promoter region, complete sequence. Accession No. AY578685):

```
  1  ctgcagtatt tagcatgccc cacccatctg caaggcattc tggatagtgt caaaacagcc 61  ggaaatcaag tccgtttatc tcaaacttta gcattttggg aataaatgat atttgctatg 121  ctggttaaat tagattttag ttaaatttcc tgctgaagct ctagtacgat aagcaacttg 181  acctaagtgt aaagttgaga tttccttcag gtttatatag cttgtgcgcc gcctgggtac 241  ctc
```

In another embodiment, the 7SK is a mutant of SEQ ID NO: 3 that improves the engraftment of GFP expressing vector modified cells in vivo in humanized BLT mice (SEQ ID NO: 4):

```
  1 ctgcagtcgg gctactgccc cacccatagt accggcattc
    tggatagtgt caaaacagcc
 61 ggaaatcaag tccgtttatc tcaaacttta gcattttggg
    aataaatgat atttgctatg
121 ctggttaaat tagattttag ttaaatttcc tgctgaagct
    ctagtacgat aagcaacttg
181 acctaagtgt aaagttgaga tttccttcag gtttatatag
    cttgtgcgcc gcctgggtac
241 ctc
```

In another embodiment, the 7SK is a mutant of SEQ ID NO: 3 that improves the engraftment of GFP expressing vector modified cells in vivo in humanized BLT mice by using some or all of the mutations shown in SEQ ID NO: 4, providing SEQ ID NO: 5:

```
  1 ctgcagtmkk kmkmmtgccc cacccatmkk mmmggcattc
    tggatagtgt caaaacagcc
 61 ggaaatcaag tccgtttatc tcaaacttta gcattttggg
    aataaatgat atttgctatg
121 ctggttaaat tagattttag ttaaatttcc tgctgaagct
    ctagtacgat aagcaacttg
181 acctaagtgt aaagttgaga tttccttcag gtttatatag
    cttgtgcgcc gcctgggtac
241 ctc
```

The invention additionally provides a pharmaceutical composition comprising a polynucleotide, or active fragment thereof, as described herein. In some embodiments, the polynucleotide, or active fragment thereof, is linked to heterologous sequence. The heterologous sequence can be selected to facilitate the use of the polynucleotide, for example, by adding a tag to facilitate detection or adding a partner that facilitates delivery or solubility. The composition optionally comprises one or more additional components that facilitate retention of biological activity of the polynucleotide and are non-reactive with the immune system. Such pharmaceutically acceptable carriers are known in the art.

Methods

The invention further provides a method for knocking down hypoxanthine guanine phosphoribosyltransferase (HPRT) in a cell, the method comprising contacting the cell with a polynucleotide of the invention under conditions permitting expression of SEQ ID NO: 1 in the cell. Also provided is a method for conferring resistance to a guanine analog antimetabolite in a cell, the method comprising contacting the cell with a polynucleotide according to the invention under conditions permitting expression of SEQ ID NO: 1 in the cell. In one embodiment, the guanine analog antimetabolite is 6-thioguanine (6TG), 6-mercaptopurine (6-MP), or azathioprine (AZA). Representative examples of cells include, but are not limited to; hematopoietic stem cells, T cells, peripheral blood mononuclear cells (PBMCs), and CD34+ cells. Those skilled in the art will appreciate other cells suitable for use with the methods described herein.

The invention also provides a method for producing selectable genetically modified cells, wherein the cells have been modified to express a gene of interest. The method comprises contacting a plurality of cells with a polynucleotide of the invention under conditions permitting expression of the gene of interest and SEQ ID NO: 1. In one embodiment, the method further comprises removing unmodified cells from the plurality of cells. The removing comprises treating the plurality of cells contacted with the polynucleotide with a guanine analog antimetabolite. In another embodiment, the method further comprises removing the genetically modified cells from the plurality of cells. In this embodiment, the removing comprises treating the plurality of cells with methotrexate (MTX).

Additionally, the invention provides a method for selecting cells genetically modified with a gene of interest. The method comprises: (a) contacting a plurality of cells that comprises genetically modified cells, wherein the genetically modified cells have been modified with a polynucleotide of the invention under conditions permitting expression of the gene of interest and SEQ ID NO: 1; and (b) removing unmodified cells from the plurality of cells. The removing comprises treating the plurality of cells contacted with the polynucleotide with a guanine analog antimetabolite.

Further provided is a method for removing cells genetically modified with a gene of interest. The method comprises: (a) contacting a plurality of cells that comprises genetically modified cells, wherein the genetically modified cells have been modified with a polynucleotide of the invention under conditions permitting expression of the gene of interest and SEQ ID NO: 1; and (b) removing the genetically modified cells from the plurality of cells. The removing comprises treating the plurality of cells with methotrexate (MTX). The MTX-mediated removal strategy provides a safety procedure to eliminate genetically modified cells in the event of unwanted side effects or other adverse events. The MTX-mediated elimination strategy can also be used for mitigating side effects of cancer immune gene therapy where genetically modified T cells with a tumor specific T cell receptor or a chimeric antigen receptor (CAR) cause unwanted side effects in a cell infused patient, such as, for example, cytokine storm syndrome, or graft versus host reaction. MTX treatment could eliminate the gene modified cells in a patient.

In a further embodiment, the invention provides a method for treating a subject infected with HIV. In one embodiment, the method comprises: (a) contacting a plurality of hematopoietic stem/progenitor cells (HSPCs) that have been modified with a polynucleotide of the invention under conditions permitting expression of the gene of interest and SEQ ID NO: 1; (b) treating the plurality of cells contacted with the polynucleotide with a guanine analog antimetabolite to form a purified population of genetically modified cells; and (c) administering the purified population of genetically modified cells to the subject. Selection with purine analogs can be titrated to the desired level of hematopoietic toxicity. If necessary, subjects can be re-dosed.

Typically, the subject is a mammal. The mammalian subject can be murine, canine, feline, bovine, equine, ovine, primate or human. In one embodiment, the subject is human.

Administration and Dosage

The compositions are administered in any suitable manner, often with pharmaceutically acceptable carriers. Suitable methods of administering treatment in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual as well as with the selected drug, and may be readily established using standard techniques. In general, the pharmaceutical compositions may be administered, by injection (e.g., intracutaneous, intratumoral, intramuscular, intravenous or subcutaneous), intranasally (e.g., by aspiration) or orally. Alternate protocols may be appropriate for individual patients.

As is understood by those skilled in the art, doses can be converted from mg/kg body weight to mg/body surface area, the latter being suitable for use with larger mammalian subjects, including humans. Calculators for allometric scaling are known in the art and readily obtained online. Generally, allometric scaling uses an exponent of 0.75-0.80. For more information, see West & Brown, J Exp Bio 208, 1575-1592, 2005. In addition, the United States Food and Drug Administration publishes "Guidance for Industry: Estimating the Maximum Safe Starting Dose in Initial Clinical Trials for Therapeutics in Adult Healthy Volunteers," which is available from: Office of Training and Communications Division of Drug Information, HFD-240 Center for Drug Evaluation and Research Food and Drug Administration 5600 Fishers Lane Rockville, Md. 20857.

For example, 5 mg/kg 6TG corresponds to a dose of 15.08 mg/m$^2$ for a 20 g mouse. This equals 0.4 mg/kg for a 65 kg human. Absorption after oral 6TG administration is estimated to be 30%, therefore this i.p. dose in mice corresponds to an absorbed dose after oral administration of about 1.3 mg/kg in humans. The conventional oral dose for 6TG single-agent chemotherapy in pediatric patients and adults is 2 mg/kg of body weight per day; if no treatment response is observed after 4 weeks, the dose can be increased to 3 mg/kg.

EXAMPLES

The following examples are presented to illustrate the present invention and to assist one of ordinary skill in making and using the same. The examples are not intended in any way to otherwise limit the scope of the invention.

Example 1

In Vivo Selection Strategy for Genetically Modified HIV Protected Hematopoietic Stem/Progenitor Cells While HSPC based anti-HIV gene therapy hold a great hope for HIV cure, previous clinical studies have met with limited success largely due to the low efficiency of hematopoietic reconstitution with anti-HIV gene modified HSPC. This example describes a novel chemoselection approach to overcome this limitation.

To improve engraftment of anti-HIV gene modified HSPC, we investigated an in vivo selection strategy that exclusively employs 6-thioguanine (6TG) for both preconditioning and chemoselection of hypoxanthine-guanine phosphoribosyltransferase (HPRT) down-regulated anti-HIV genetically engineered HSPC, that is capable of enriching engraftment and long-term reconstitution of genetically engineered anti HIV modified HSPC and progenies. To provide 6TG resistance to gene-modified cells, we have identified an HPRT short hairpin RNA (shRNA) that enables 6TG-mediated positive selection of lentiviral vector-transduced HPRT knockdown human T-cell line, CD34+ cells and primary peripheral blood mononuclear cells (PBMC) in vitro. Our in vivo engraftment experiment of CCR5 shRNA and HPRT shRNA co-expressing vector modified human HSPC shows reconstitution of CCR5 down-regulated human T-cells in humanized BLT mice. Ex vivo isolated vector modified splenocytes from the BLT mice were positively selected by 6TG. These results demonstrate that our newly developed HPRT shRNA can be combined with our CCR5 directed shRNA in a lentiviral vector for positive selection.

In addition to the positive selection, a novel feature of the present HPRT knockdown strategy is that it can be used as a negative selection to eliminate the HPRT knockdown gene modified cells by a clinically available methotrexate (MTX) by inhibiting the enzyme dihydrofolate reductase (DHFR) in the purine de novo synthetic pathway. MTX negatively selected against human T-cell line and CD34+ cells expressing HPRT shRNA in vitro. Thus, it can be developed as a safety procedure to eliminate gene modified HSPC in case of unexpected adverse effects observed.

The novel in vivo chemoselection strategy described herein improves the efficiency of anti-HIV gene-modified cell engraftment and provides a treatment for HIV. 6-thioguanine (6TG) chemotoxin-resistance is accomplished by lentiviral vector-mediated delivery of a short hairpin RNA (shRNA) targeting hypoxanthine-guanine phosphoribosyltransferase (HPRT), an enzyme which is required for a purine analog, such as 6TG, to exert its cytotoxic effects. shRNAs are small (20-22 nt) and can be co-expressed from a lentiviral vector without significantly affecting vector titer. Combination with other anti-HIV genes to develop multipronged anti-HIV vectors is therefore feasible.

Figure 4:
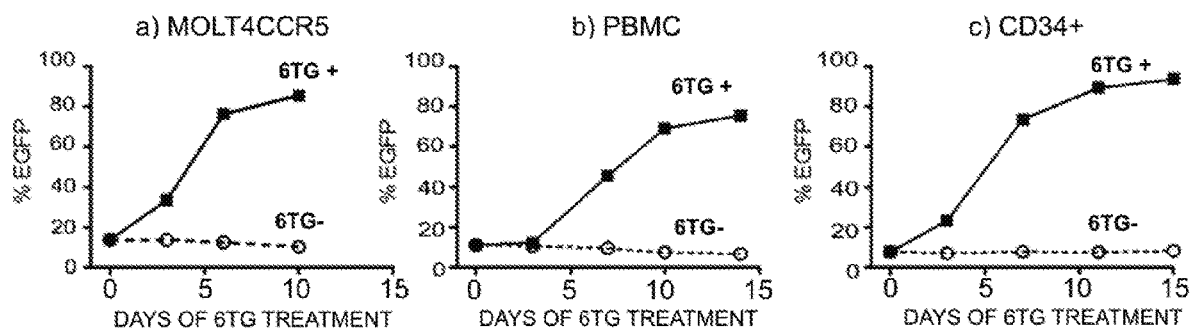
FIG. 4. Lentiviral vector delivery of HPRT shRNA results in efficient selections of HPRT knockdown by 6TG. Selection of HPRT knockdown Molt4-CCR5, PBMC and CD34+ cell by 6TG. The shRNA vector and control vector transduced cells were cultured with or without 6TG.
Figure 5:
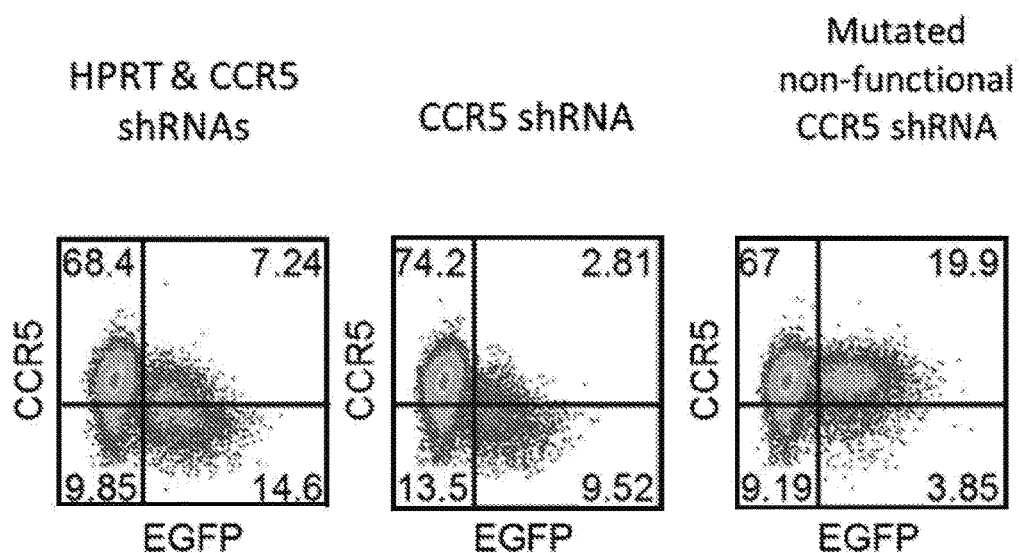
FIG. 5. CCR5 down-regulate in Molt4CCR5 cells.
Figure 6:
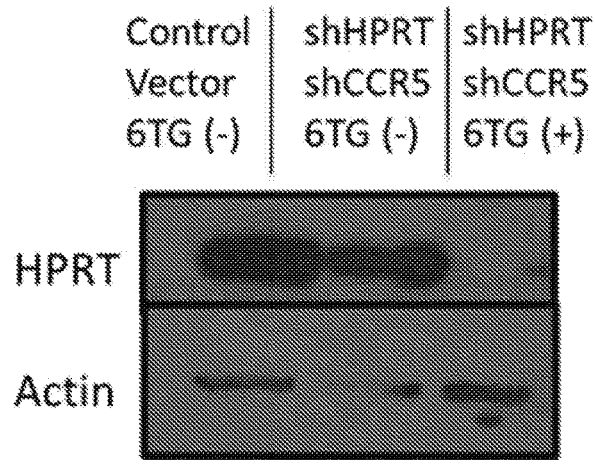
FIG. 6. HPRT knockdown in vector transduced cells. Whole cell lysates were analyzed by Western blot after transduction at the indicated time points.

Positive selection of HPRT knock down cells by 6TG is illustrated in FIGS. 4-6, which show that lentiviral vector delivery of HPRT shRNA results in efficient selections of HPRT knockdown by 6TG. As shown in FIG. 4, selection of HPRT knockdown Molt4-CCR5, PBMC and CD34+ cell by 6TG. The shRNA vector and control vector transduced cells were cultured with or without 6TG. FIG. 5 shows that CCR5 is down-regulated in Molt4CCR5 cells. Whole cell lysates were analyzed by Western blot after transduction at the indicated time points. HPRT knockdown in vector transduced cells is shown in FIG. 6.

Figure 7:
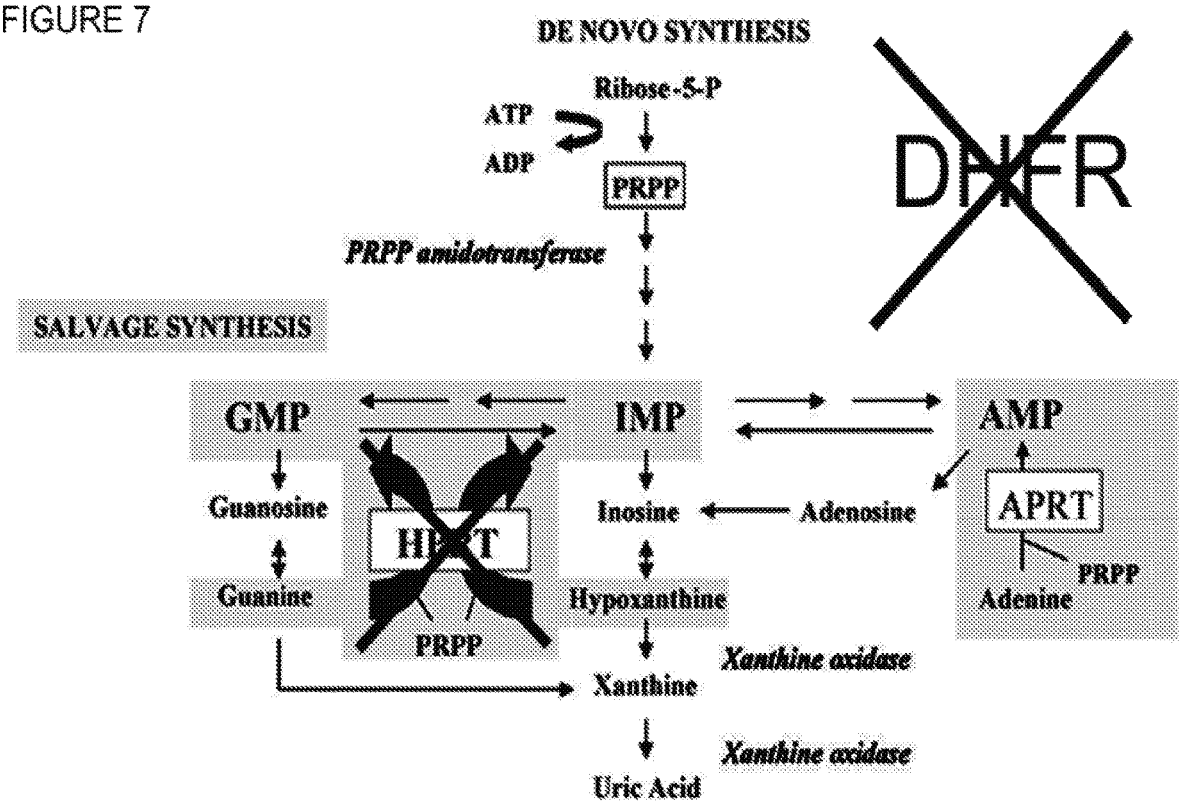
FIG. 7. Schematic illustration of elimination of HPRT knock down gene modified cells by MTX for safety.

Negative selection of HPRT knock down cells by MTX is illustrated in FIG. 7, which presents a schematic illustration of MTX mediated inhibition of Dihydrofolate reductase (DHFR) induced cell death in HPRT knock down cells. The metabolic scheme shows the first and rate-limiting step of de novo purine synthesis mediated by the enzyme 5'-phosphoribosyl-1-pyrophosphate (PRPP) amidotransferase, and the salvage pathway mediated by hypoxanthine phosphorybosyltransferase (HPRT) and adenine phosphorybosyltransferase (APRT). The de novo synthesis occurs through a multi-step process and requires the contribution of four aminoacids, one PRPP, two folates and three ATP to synthesize an inosine monophosphate (IMP) molecule. HPRT catalyzes the salvage synthesis of inosine monophosphate (IMP) and guanosine monophosphate (GMP) from the purine bases hypoxanthine and guanine respectively, utilizing PRPP as a co-substrate. The HPRT defect results in the accumulation of its substrates, hypoxanthine and guanine, which are converted into uric acid by means of xanthine oxidase. Elevated APRT activity may also contribute to purine overproduction.

Figure 8:
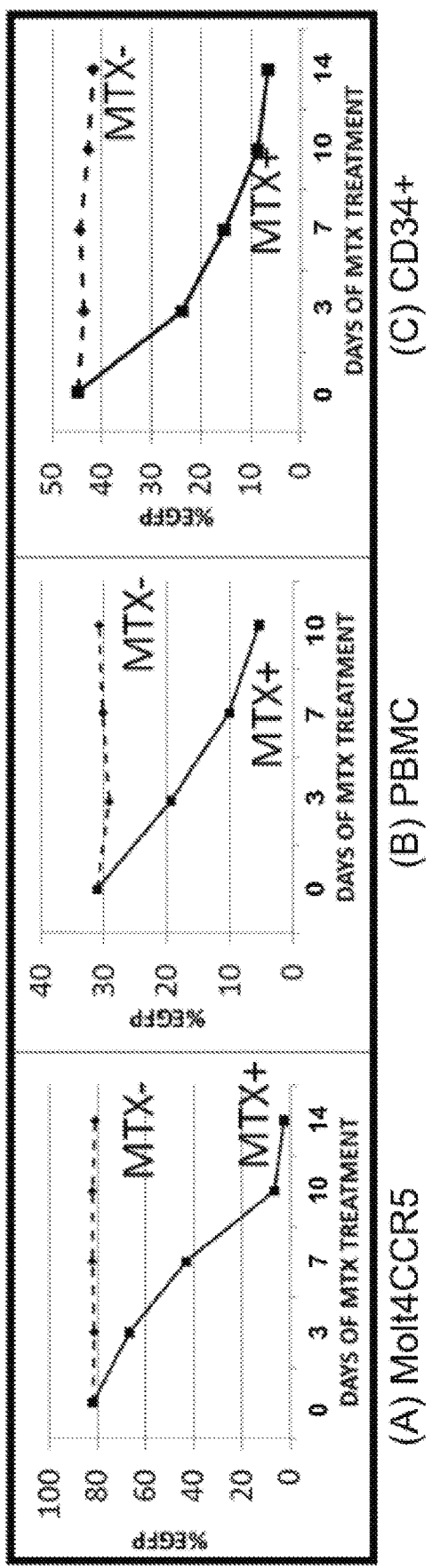
FIG. 8. Line graphs showing MTX mediated inhibition of Dihydrofolate reductase (DHFR) induced cell death in HPRT knock down cells.

Results of MTX mediated negative selection of HPRT/CCR5 knock down gene modified cells is shown in FIG. 8. Molt4CCR5 (A), PBMC (B) and CD34+ (C) cells were transduced with dual shRNA vector. The transduced cells were cultured with or without 10 µM MTX. Cells were monitored for % EGFP and given fresh media containing MTX every 3 days.

Figure 9:
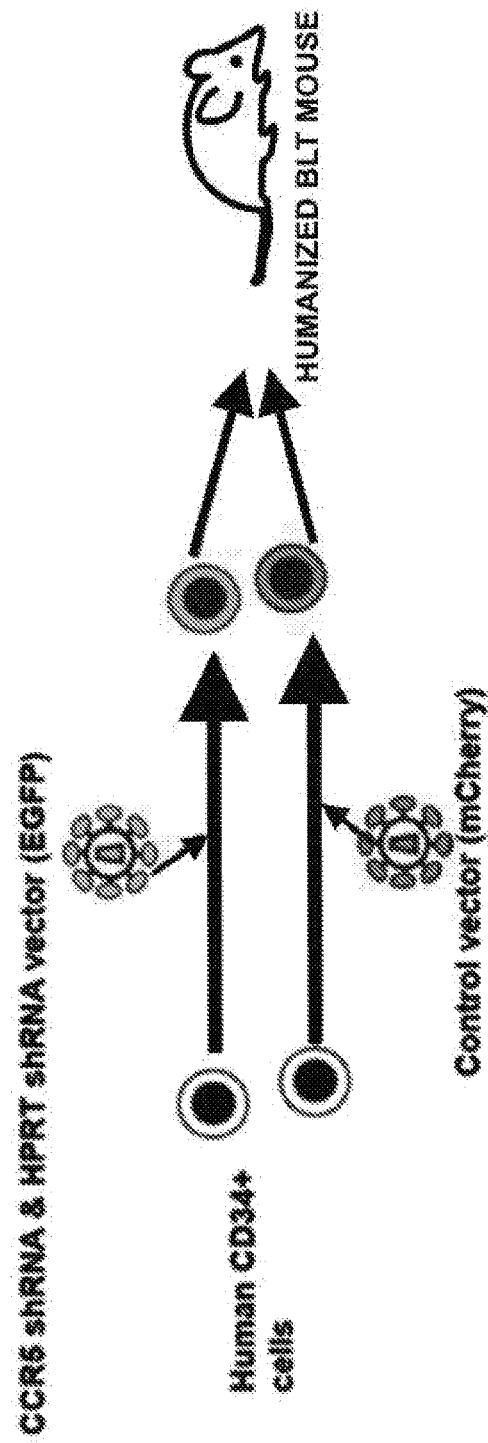
FIG. 9. Improved engraftment of HPRT/CCR5 shRNA vector transduced CD34+ hematopoietic stem/progenitor cells in using the BLT humanized mouse model. Human fetal liver derived CD34+ cells are transduced with either dual shRNA vectors (HPRT shRNA & CCR5 shRNA) or control vector separately. Dual shRNA and control vector transduced cells were mixed 1:1 ratio and transplant into NSG mice with human thymus in kidney capsule and intravenously.
Figure 10:
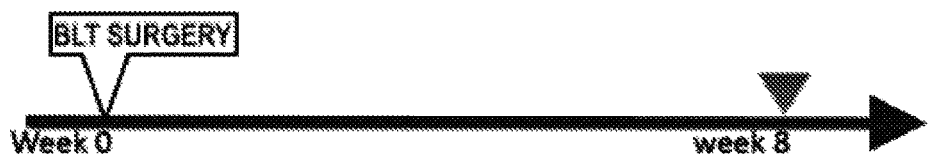
FIG. 10. Treatment group was injected 6TG from a week after surgery, as illustrated in timelines. The graphs show percentage of marker (EGFP or mCherry) in human CD45+ cells in mouse PBMC that was measured by FACS at week 0 (left graph) and at 8 weeks after surgery (right graph).
Figure 10:
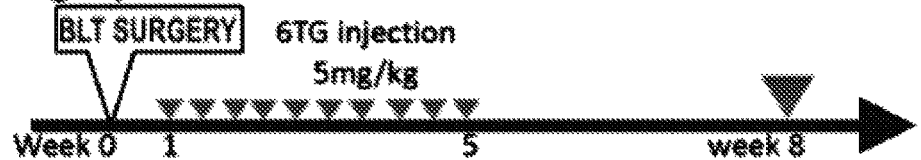
Figure 10:
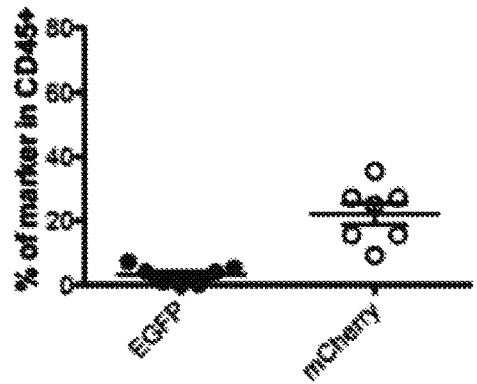
Figure 10:
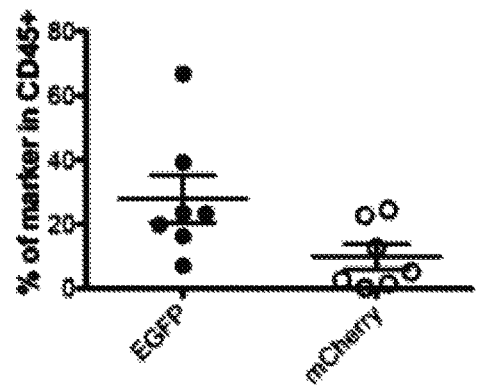

In vivo selection of HPRT knock down CD34+ hematopoietic stem/progenitor cells is shown in FIGS. 9 and 10. FIG. 9 illustrates the engraftment of HPRT/CCR5 shRNA vector transduced CD34+ hematopoietic stem/progenitor cells in BLT hu mouse model. Human fetal liver derived CD34+ cells are transduced with either dual shRNA vectors (HPRT shRNA & CCR5 shRNA) or control vector separately. Dual shRNA and control vector transduced cells were mixed 1:1 ratio and transplant into NSG mice with human thymus in kidney capsule and intravenously.

As illustrated in FIG. 10, the treatment group was injected with 6TG from a week after surgery, per the timelines. The graphs show percentage of marker (EGFP or mCherry) in human CD45+ cells in mouse PBMC that was measured by FACS at week 0 (left graph) and at 8 weeks after surgery (right graph).

Lentiviral vector delivery of HPRT shRNA and CCR5 shRNA resulted in efficient HPRT and CCR5 co-knockdown and conferred ability to positively select EGFP+ vector transduced cells by 6TG. Vector transduced HPRT knock down cells are negatively selected by MTX. The engraftment of HPRT/CCR5 shRNA vector transduced human fetal liver CD34+ HSPC had 5-fold increase in 6TG treated group than untreated group in vivo in humanized BLT mice.

Figure 11:
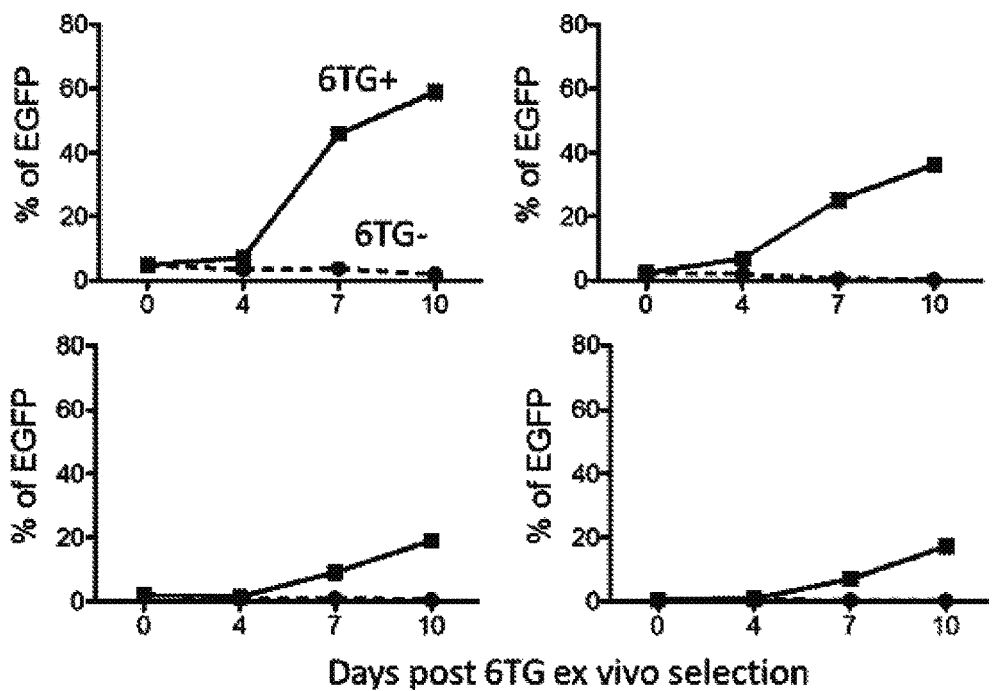
FIG. 11. Graphs demonstrating ex vivo selection of vector modified splenocytes from BLT mice.

The ex vivo selection of vector modified splenocytes from BLT mice is shown in FIG. 11. Transduction efficiency in CD34+ was 15.6%. Isolated mouse splenocytes were cultured with and without 0.3 µM 6TG.

Example 2

Improved Promoter for Use with HPRT shRNA

This example describes a mutant 7SK RNA promoter that improves the stability of GFP expressing vector modified cells in vivo in humanized BLT mice. The novel promoter has the sequence shown in SEQ ID NO: 4.

Due to an observed slight decline of in vivo 6TG selected vector marked EGFP+ human CD45+ lymphoid cells in the peripheral blood from 8 to 14 weeks post vector transduced CD34+ HSPC transplant in humanized BLT mice, we developed a more stable 6TG selectable anti HIV-1 lentiviral vector. We hypothesized that the simultaneous two short hairpin RNA (CCR5sh1005 and HPRTsh734) expression might negatively affect the cell growth of transplanted vector transduced CD34+ HSPC and progeny cells in humanized BLT mice. This hypothesis is based on our previous experience that over expression of shRNA from a strong RNA polymerase promoter III such as U6 can cause cytotoxicity in human T lymphocytes and reducing shRNA expression using a weaker promoter (H1) can minimize the cytotoxic effects (An. D S., et. al. Molecular Therapy 2006). Other possibilities could be that efficient HPRT down regulation itself might have a negative impact on cell growth.

Figure 12:
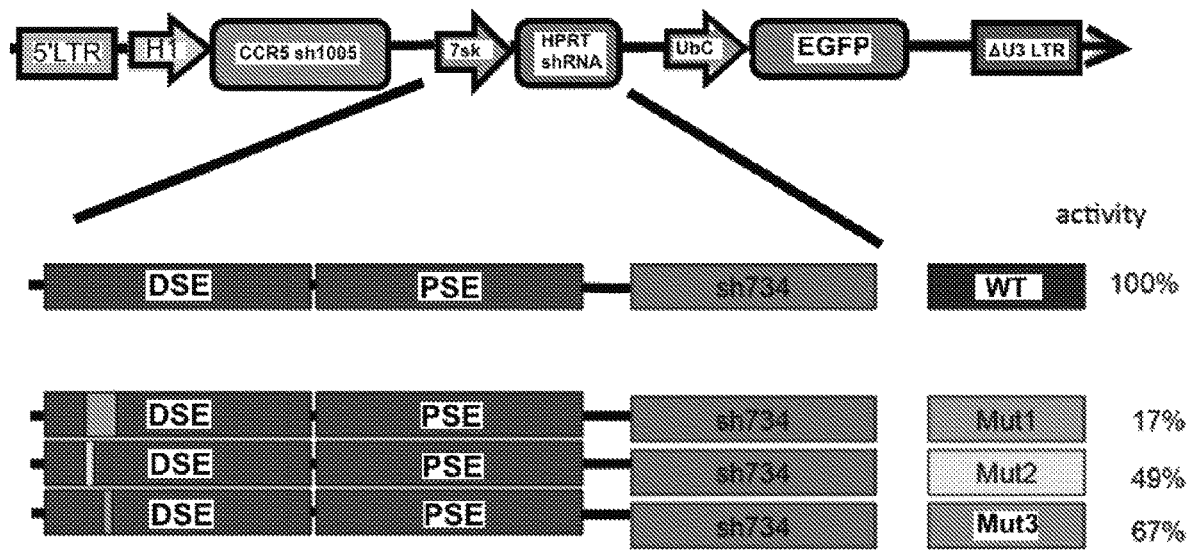
FIG. 12. Schematic diagram of chemoselectable anti-HIV gene lentiviral vector with mutated 7SK promoter. Mutations were introduced in the distal sequence element (DSE) of the 7SK RNA polymerase III promoter to reduce HPRTsh734 expression. The vector also expresses anti CCR5 shRNA sh1005 and EGFP. As indicated in the diagram, the mutant promoter exhibits 17% of the activity of the wild type 7SK promoter.

To improve the stability of vector modified cells, we hypothesized that reducing the level of HPRT shRNA expression might mitigate these negative effects. To test our hypothesis, we developed three lentiviral vectors that express HPRTshRNA 734 from attenuated 7SK promoters with mutations in the distal sequence element (DSE) (Mutant1, Mutant2 and Mutant3) (FIG. 12). Based on previous work, Mutant1, Mutant2 and Mutant3 are expected to lower HPRTsh734 expression at 17%, 49% and 67% when transfected in HeLa cells, respectively (Boyd D C, et al. J Mol Biol. 1995 Nov. 10;253(5):677-90). The level of HPRT shRNA734 is currently measured by a quantitative siRNA PCR assay. Based on our results and the literature (Boyd D C, et al.), the vector with Mutant1 is expected to express HPRTshRNA 734 at the lowest level. It was not known if Mutation1 could reduce sh734 expression in human HSPCs and T lymphocytes. Therefore, we further tested the vector in vitro and 6TG mediated selection. The vector transduced human CCRT MT4 cell line was efficiently selected with 6TG in vitro.

We observed improved in vivo positive selection of vector modified human hematopoietic cells with the newly developed vector with 7SK mutation1 in humanized BLT mice. BLT mice were reconstituted with CD34+ HSPC with the vector with Mutation1 in the 7SK promoter. Mice were treated with 6TG once a week for a total of 8 times or no treatment. Peripheral blood derived human CD45+, CD3+, CD4 and CD8+ lymphocytes were analyzed for EGFP expression at 9 week post time point.

Figure 13:
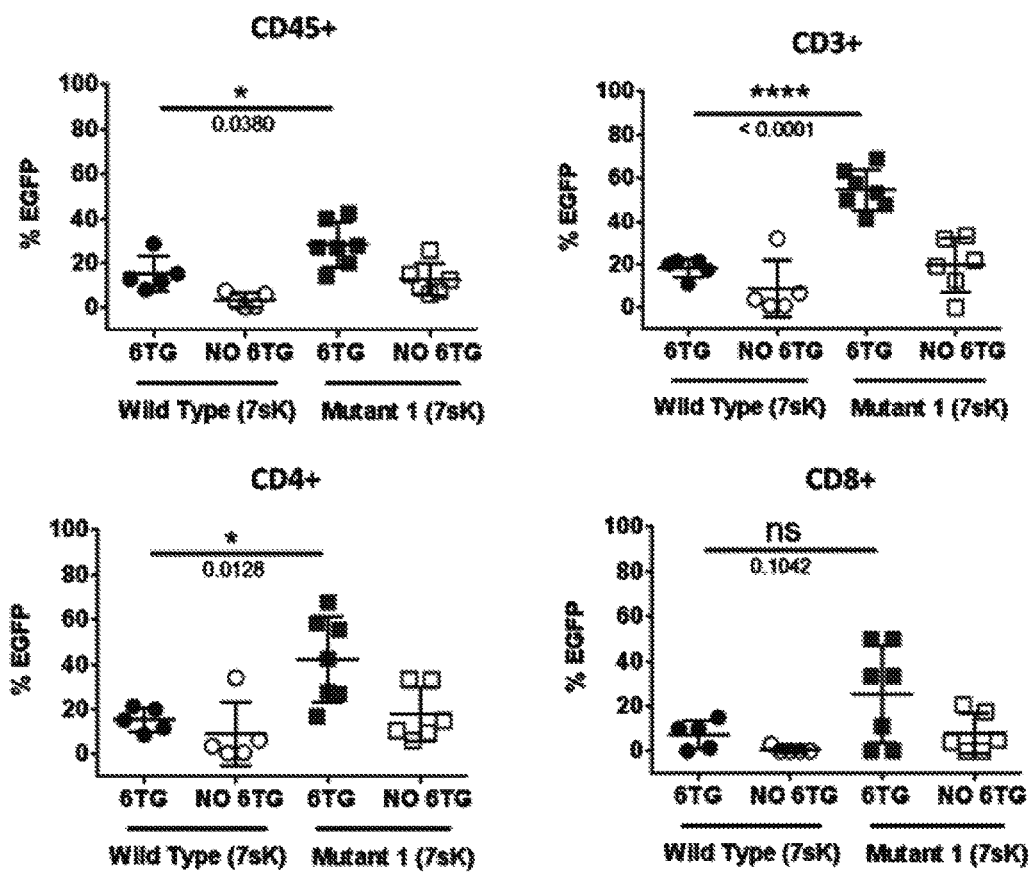
FIG. 13. Improved in vivo positive selection of vector modified human hematopoietic cells with the newly developed vector with 7SK mutation1 in humanized BLT mice. BLT mice were reconstituted with CD34+ HSPC with the vector with Mutation1 in the 7SK promoter. Mice were treated with 6TG once a week for a total of 8 times or no treatment. Peripheral blood derived human CD45+, CD3+, CD4 and CD8+ lymphocytes were analyzed for EGFP expression at 9 week post time point.

Results from this experiment show significantly higher (p value <0.05) vector marked EGFP+ human CD45+, CD3+ and CD4+ lymphocytes in the peripheral blood with the newly developed vector than the previous vector (FIG. 13).

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A polynucleotide comprising a nucleic acid sequence encoding a short hairpin ribonucleic acid molecule 734 (shRNA734), wherein the shRNA734 comprises the sequence of SEQ ID NO: 1.

2. The polynucleotide of claim 1, further comprising an expression control sequence.

3. The polynucleotide of claim 2, which is a viral vector.

4. The polynucleotide of claim 2, formulated as a pharmaceutical composition.

5. The polynucleotide of claim 2, wherein the expression control sequence comprises a 5' long terminal repeat (LTR) upstream of the shRNA734 and a 3' LTR downstream of the shRNA734.

6. The polynucleotide of claim 5, further comprising a gene of interest disposed downstream of the 5' LTR and upstream of the 3' LTR.

7. The polynucleotide of claim 6, wherein the gene of interest is a therapeutic gene.

8. The polynucleotide of claim 6, wherein the gene of interest comprises up to 3 or 4 genes in series.

9. The polynucleotide of claim 6, wherein the gene of interest is an inhibitor of CCR5.

10. The polynucleotide of claim 9, wherein the gene of interest comprises the sequence of SEQ ID NO: 2 (CCR5shRNA).

11. The polynucleotide of claim 10, comprising in order from 5' to 3':
    a 5' LTR;
    a human H1 RNA promoter;
    a CCR5shRNA (SEQ ID NO: 2);
    a 7SK RNA promoter;
    an shRNA734 (SEQ ID NO: 1);
    a human ubiquitin promoter;
    a second gene of interest; and
    a 3' LTR;
    wherein the second gene of interest is a green fluorescent protein or a C46 HIV fusion inhibitor.

12. The method of claim 11, wherein the 7SK comprises a sequence selected from the group consisting of SEQ ID NO: 3, SEQ ID NO: 4, and SEQ ID NO: 5.

13. A method for knocking down hypoxanthine guanine phosphoribosyltransferase (HPRT) in a cell, the method comprising contacting the cell with a polynucleotide according to claim 2 under conditions permitting expression of SEQ ID NO: 1 in the cell.

14. The method of claim 13, wherein the expression of SEQ ID NO: 1 is sufficient to confer resistance to a guanine analog antimetabolite in the cell.

15. The method of claim 14, wherein the guanine analog antimetabolite is 6-thioguanine (6TG).

16. The method of claim 14, wherein the polynucleotide further comprises a gene of interest disposed downstream of the 5' LTR and upstream of the 3' LTR, and wherein the cell with resistance to the guanine analog antimetabolite is a genetically modified cell selectable from among a plurality of cells.

17. The method of claim 16, further comprising selecting the genetically modified cells by removing unmodified cells from the plurality of cells, wherein the removing comprises treating the plurality of cells contacted with the polynucleotide with the guanine analog antimetabolite.

18. The method of claim 16, further comprising selecting the unmodified cells by removing the genetically modified cells from the plurality of cells, wherein the removing comprises treating the plurality of cells with methotrexate (MTX).

19. A method for treating a subject in need of HSPC transplantation, the method comprising:
    (a) providing a plurality of hematopoietic stem/progenitor cells (HSPCs) that have been modified with a polynucleotide of claim 5 under conditions permitting expression of the gene of interest and SEQ ID NO: 1;
    (b) treating the plurality of cells contacted with the polynucleotide with a guanine analog antimetabolite to form a purified population of genetically modified cells; and
    (c) administering the purified population of genetically modified cells to the subject.

20. The method of claim 19, wherein the subject is infected with HIV, and wherein the polynucleotide comprises an inhibitor of CCR5.

* * * * *